US012599375B2

(12) United States Patent
Kato et al.

(10) Patent No.: US 12,599,375 B2
(45) Date of Patent: Apr. 14, 2026

(54) MEDICAL MATERIAL

(71) Applicant: GUNZE LIMITED, Ayabe (JP)

(72) Inventors: Yuuki Kato, Ayabe (JP); Hinami Nakamura, Ayabe (JP)

(73) Assignee: GUNZE LIMITED, Ayabe (JP)

( * ) Notice: Subject to any disclaimer, the term of this patent is extended or adjusted under 35 U.S.C. 154(b) by 89 days.

(21) Appl. No.: 18/686,726

(22) PCT Filed: Aug. 22, 2022

(86) PCT No.: PCT/JP2022/031502
§ 371 (c)(1),
(2) Date: Feb. 26, 2024

(87) PCT Pub. No.: WO2023/027005
PCT Pub. Date: Mar. 2, 2023

(65) Prior Publication Data
US 2025/0025144 A1 Jan. 23, 2025

(30) Foreign Application Priority Data
Aug. 27, 2021 (JP) ................................. 2021-138761

(51) Int. Cl.
A61B 17/00 (2006.01)
(52) U.S. Cl.
CPC .................... A61B 17/0057 (2013.01); *A61B 2017/00004* (2013.01); *A61B 2017/00597* (2013.01);
(Continued)
(58) Field of Classification Search
CPC ...... A61B 17/0057; A61B 2017/00575; A61B 2017/00606; A61B 2017/00615; A61B 2017/00619
See application file for complete search history.

(56) References Cited

U.S. PATENT DOCUMENTS

2005/0273135 A1* 12/2005 Chanduszko ...... A61B 17/0057
606/213
2009/0018562 A1 1/2009 Amplatz et al.
(Continued)

FOREIGN PATENT DOCUMENTS

JP 2009-18150 A 1/2009
JP 2019-16472 A 1/2019
(Continued)

OTHER PUBLICATIONS

International Search Report, issued in PCT/JP2022/031502, PCT/ISA/210, dated Nov. 8, 2022.

*Primary Examiner* — Todd J Scherbel
(74) *Attorney, Agent, or Firm* — Birch, Stewart, Kolasch & Birch, LLP

(57) ABSTRACT

A medical material makes it possible to perform less invasive treatment of atrial septal defect and is unlikely to cause problems in the late post-treatment period. A medical material includes a substantially middle portion and two tubular portions (first tubular portion, second tubular portion) having a mesh structure formed of a bioabsorbable linear material and includes a proximal connecting part connected to a first end and a distal connecting part connected to a second end and threaded to a delivery cable. The proximal connecting part and the distal connecting part are configured to reversibly or irreversibly achieve a locked state and an unlocked state, the locked state being a state in which the proximal connecting part and the distal connecting part remain united, the unlocked state being a state in which the proximal connecting part and the distal connecting part do not remain united. When the distal connecting part is inserted into the proximal connecting part, the engaging portion of the distal connecting part engages with the engaged portion of the proximal connecting part to cause the
(Continued)

medical material to transition from the unlocked state to the locked state.

1 Claim, 16 Drawing Sheets

(52) U.S. Cl.
CPC .............. *A61B 2017/00601* (2013.01); *A61B 2017/00623* (2013.01)

(56) References Cited

U.S. PATENT DOCUMENTS

| | | |
|---|---|---|
| 2011/0307000 A1 | 12/2011 | Amplatz et al. |
| 2013/0218189 A1 | 8/2013 | Amplatz et al. |
| 2018/0103956 A1 | 4/2018 | Sakamoto et al. |
| 2021/0169497 A1 | 6/2021 | Sakamoto et al. |
| 2022/0218321 A1 | 7/2022 | Kurobe et al. |

FOREIGN PATENT DOCUMENTS

| | | |
|---|---|---|
| JP | 2021-16478 A | 2/2021 |
| JP | 2021-53267 A | 4/2021 |
| WO | WO 2016/174972 A1 | 11/2016 |
| WO | WO 2019/208822 A1 | 10/2019 |
| WO | WO 2020/012728 A1 | 1/2020 |

\* cited by examiner

MEDICAL MATERIAL

TECHNICAL FIELD

The present invention relates to a medical material to treat a hole in biological tissue, and particularly relates to a medical material to be set in a catheter, sent to a treatment site through a blood vessel, and placed in a living body.

BACKGROUND ART

The heart of a human is divided into left and right chambers by tissue called the septum, and each of the left and right chambers has an atrium and a ventricle. That is, the heart is composed of two atria and two ventricles, i.e., right atrium, right ventricle, left atrium, and left ventricle. With regard to the heart having such a structure, atrial septal defect (ASD) is known, which is a defect wherein, due to a disorder of development in the fetal period, there is a congenital hole called a hole in the atrial septum separating the right atrium and the left atrium.

Treatment for atrial septal defect can be performed by the following two methods. One is a surgical operation performed by opening the chest, and the other is catheterization using an occluder without opening the chest.

A surgical operation (patching operation) involves using cardiopulmonary bypass, opening the chest, and closing the hole with a patch. Catheterization involves setting an occluder in a catheter, inserting the catheter into a blood vessel, sending the catheter to a target position (the position of a hole), and then releasing the occluder to place it in the body. The catheterization is to close a hole without opening the chest, by sending a small jig (device) called an occluder, folded in an elongated shape, from a vein (femoral vein) at the groin to the position of the hole in the atrial septum. The catheterization is advantageous in that the treatment can be performed merely by making a tiny skin incision (a few millimeters) in the groin (inguinal region), which is an inconspicuous area, without having to perform open chest surgery requiring general anesthesia.

Japanese Unexamined Patent Application Publication No. 2021-053267 (Patent Literature 1) discloses a medical material which is suitable for such catheterization, which makes it possible to perform less invasive catheterization capable of releasing and placing the medical material at a treatment site inside a living body with easy and reliable operation without a complicated structure, and which is unlikely to cause problems in the late post-treatment period even when remaining in the body.

CITATION LIST

Patent Literature

PTL 1: Japanese Unexamined Patent Application Publication No. 2021-053267

SUMMARY OF INVENTION

Technical Problem

A patching operation has an issue in that it involves usage of cardiopulmonary bypass, is highly invasive, and therefore requires long hospitalization. Catheterization is preferable because it does not involve usage of cardiopulmonary bypass, is less invasive, and therefore requires only short hospitalization.

The medical material disclosed in Patent Literature 1 is a device developed and applied for by the applicant of the present application and has been well received. It is noted here that the medical material disclosed in Patent Literature 1 is comprised of two tubular bodies having a mesh structure (a first tubular portion and a second tubular portion), includes a proximal connecting part connected to a first end and a distal connecting part connected to a second end and screwed to a delivery cable, and is capable of selectively achieving: "locked" in which the proximal connecting part and the distal connecting part remain united; and "unlocked" in which the proximal connecting part and the distal connecting part do not remain united. There is still room for improvement in the operability of this transition from the unlocked state to the locked state (and vice versa).

The present invention was made in view of the medical material disclosed in Patent Literature 1 disclosed as related art, and its object is to provide a medical material which makes it possible to perform less invasive catheterization capable of releasing and placing the medical material at a treatment site inside a living body with easy and reliable operation without a complicated structure and which is unlikely to cause problems in the late post-treatment period even when remaining in the body.

Solution to Problem

In order to attain the above object, a medical material according to the present invention provides the following technical solutions.

Specifically, a medical material according to the present invention includes a tubular body having a mesh structure formed of a bioabsorbable linear material and including a substantially middle portion and two tubular portions, the two tubular portions including a first tubular portion and a second tubular portion between which the substantially middle portion is provided, wherein the substantially middle portion is smaller in tube diameter than other portions, the first tubular portion with a first end and the second tubular portion with a second end are arranged with the substantially middle portion therebetween, the first end and the second end being opposite ends in a longitudinal direction of the tubular body, when the medical material is contained in a catheter such that the first end and the second end are away from each other with the substantially middle portion therebetween and that the other portions have a reduced tube diameter, the second end is located on the same side of the catheter as a distal end of the catheter, the medical material includes a proximal connecting part connected to the mesh structure at the first end, and a distal connecting part connected to the mesh structure at the second end, the proximal connecting part is substantially in a shape of a hollow cylinder, the distal connecting part is substantially in a shape of a cylinder, the proximal connecting part and the distal connecting part are configured such that the cylinder of the distal connecting part is insertable into the hollow cylinder of the proximal connecting part, and are configured to reversibly or irreversibly achieve a locked state and an unlocked state, the locked state being a state in which the proximal connecting part and the distal connecting part remain united, the unlocked state being a state in which the proximal connecting part and the distal connecting part do not remain united, an inner diameter of the proximal connecting part is larger than an outer diameter of a delivery cable to be inserted into the catheter, the distal connecting part is configured to selectively achieve a connected state in which the distal connecting part is connected to a distal end of the delivery cable and a disconnected state in which the distal connecting part is not connected to the distal end of the delivery cable, the medical material is configured to allow the delivery cable, which has the distal end thereof connected to the distal connecting part, to extend through the substantially middle portion, be inserted into the hollow cylinder of the proximal connecting part, and extend out of the medical material in a direction from the second end to the first end, the distal connecting part includes a radially outer portion larger than an outer diameter of the delivery cable and smaller than the inner diameter of the proximal connecting part, and an engaging portion larger than an outer diameter of the radially outer portion, the proximal connecting part includes a radially inner portion which fits the radially outer portion, and an engaged portion which is larger than an inner diameter of the radially inner portion and which fits the engaging portion, and when the distal connecting part is inserted into the proximal connecting part, the engaging portion of the distal connecting part engages with the engaged portion of the proximal connecting part to cause a transition from the unlocked state to the locked state.

Preferably, the proximal connecting part may be configured to have expandability such that the inner diameter of a portion closer to the distal connecting part than the other portion of the proximal connecting part expands when the engaging portion is inserted into the radially inner portion and that the expanded inner diameter is de-expanded when the engaging portion engages with the engaged portion.

Further preferably, the proximal connecting part, which is substantially in the shape of the hollow cylinder, may be configured to achieve the expandability thereof by having one or more grooves which connect outer and inner surfaces of the hollow cylinder and which extend along a longitudinal direction of the delivery cable from an end face facing the distal connecting part to a predetermined location short of an end face at the first end.

Further preferably, the predetermined location may be a location closer to the first end, which is a proximal end, than the engaged portion is.

Further preferably, the engaging portion and/or the engaged portion may have a shape to provide a greater resistance to relative movement of the proximal connecting part and the distal connecting part during a transition from the locked state to the unlocked state in which the distal connecting part is removed from the proximal connecting part than during a transition from the unlocked state to the locked state in which the distal connecting part is inserted into the proximal connecting part.

More preferably, the shape may be configured such that a proximal portion which is a portion closer to the first end is smoother in shape than a distal portion which is a portion closer to the second end.

More preferably, the shape may be configured such that the proximal portion which is a portion closer to the first end includes a curved shape, and the distal portion which is a portion closer to the second end includes a flat shape.

Advantageous Effects of Invention

A medical material according to the present invention makes it possible to perform less invasive catheterization capable of releasing and placing the medical material at a treatment site in a living body with easy and reliable operation without a complicated structure. Furthermore, the medical material according to the present invention is unlikely to cause problems in the late post-treatment period even when remaining in the body.

DESCRIPTION OF EMBODIMENTS

The following description discusses a medical material according to the present invention in detail with reference to the drawings. Although the following description discusses an occluder (which may be referred to as a medical material 100) for use in catheterization as an example of the medical material according to the present invention, the medical material according to the present invention is suitably applicable also to closure of other openings or passageways including, for example, other openings in the heart such as ventricular septal defect and patent ductus arteriosus and openings or passageways in other parts of a living body (for example, stomach) such as arteriovenous fistula. As such, the occluder (medical material 100) according to an embodiment of the present invention is not limited to be used for the closure of a hole of atrial septal defect.

Moreover, although the description in the following embodiment is based on the assumption that a mesh structure of a medical material 100 which is an example of a medical material according to the present invention is knitted or woven from bioabsorbable (which is synonymous with biodegradable and bioerodible) fiber (an example of a linear material), the present invention is not limited thereto. It is only necessary that the medical material according to the present invention be an occluder (medical material 100) to enable catheterization to close a hole in a living body, and its mesh structure and material are not limited. For example, the material may be knitted or woven from a linear material other than the bioabsorbable fiber. Such a linear material is preferably a linear material having a certain degree of hardness to achieve form retaining property (shape retaining property) of the occluder (medical material 100).

Figure 1:
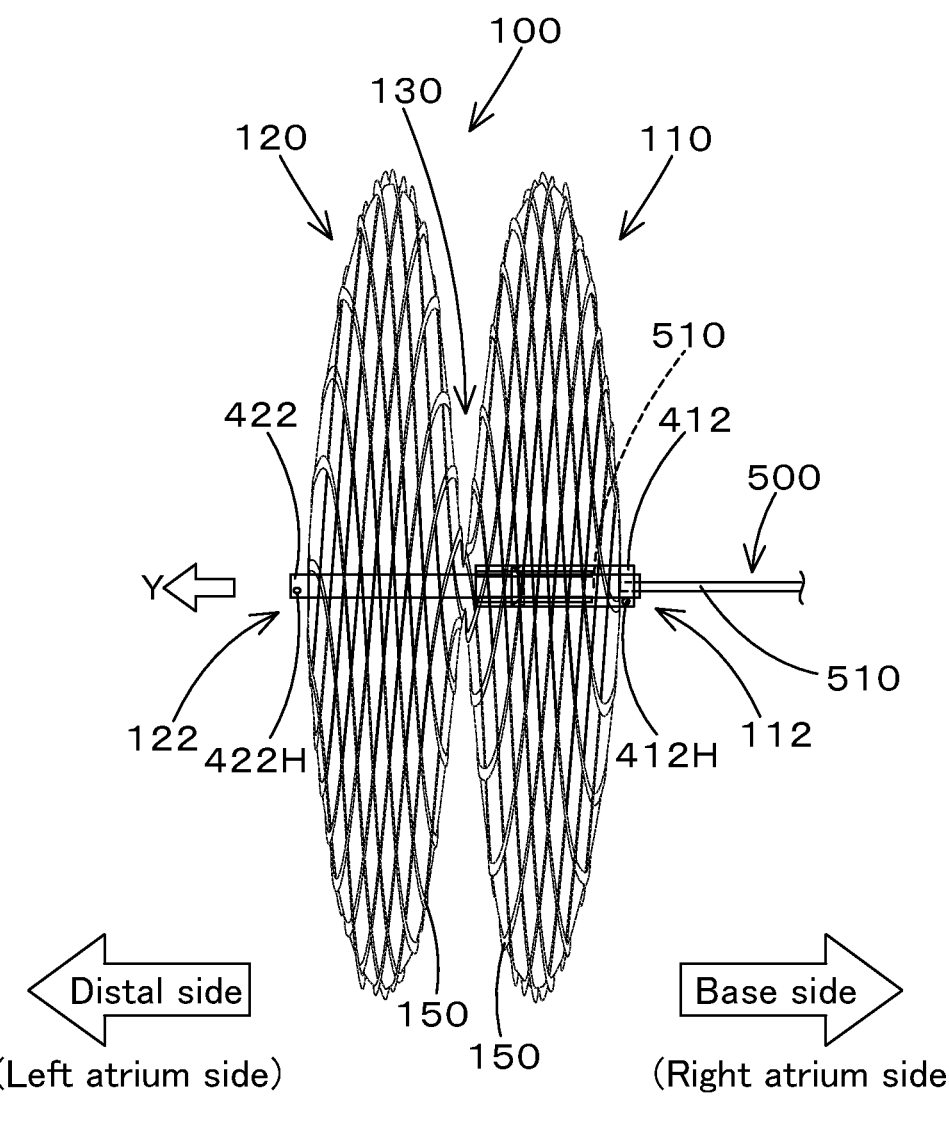
FIG. 1 is an overall view of a medical material 100 which is an example of a medical material according to the present invention (in the state in which a first end and a second end are close to each other).
Figure 2:
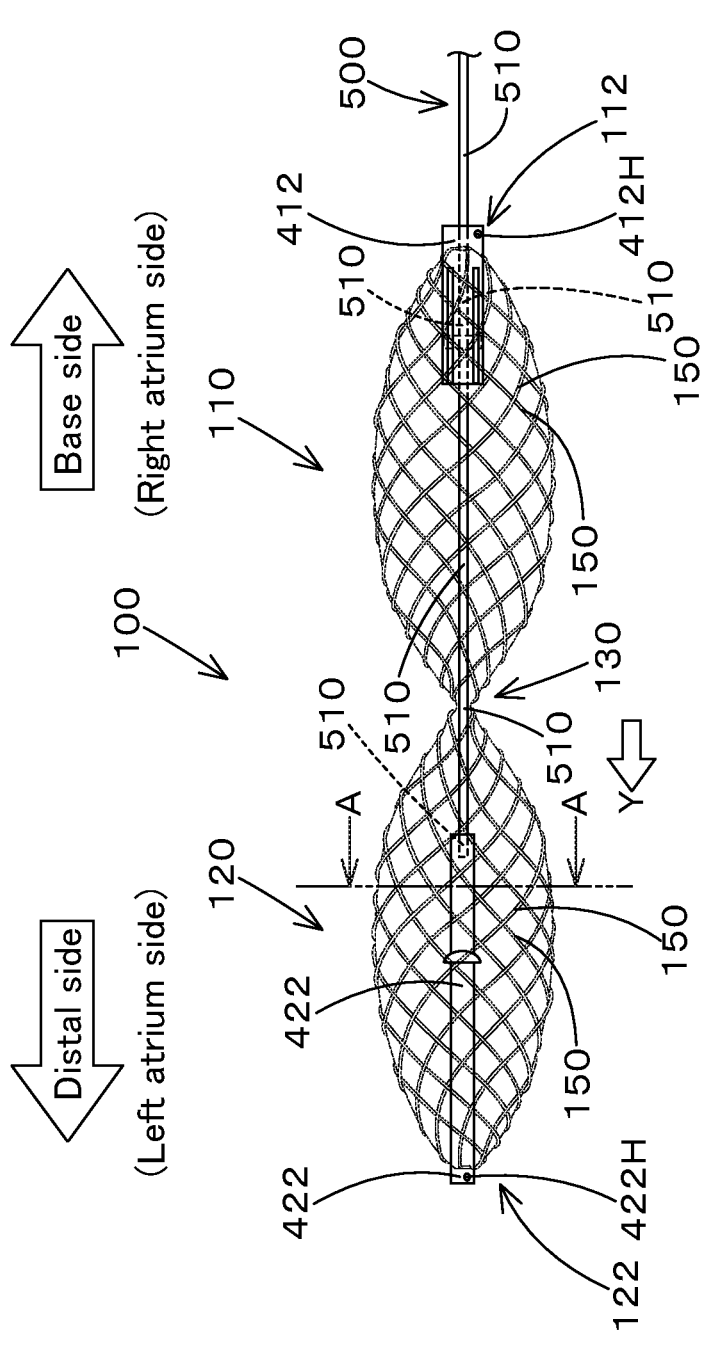
FIG. 2 is an overall view of a medical material 100 (the distance between the first end and the second end is in an intermediate state).
Figure 3:
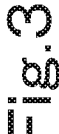
FIG. 3 is an overall view of a medical material 100 (the medical material 100 is entirely contained in a catheter 300 and the first end and the second end are away from each other).
Figure 3:
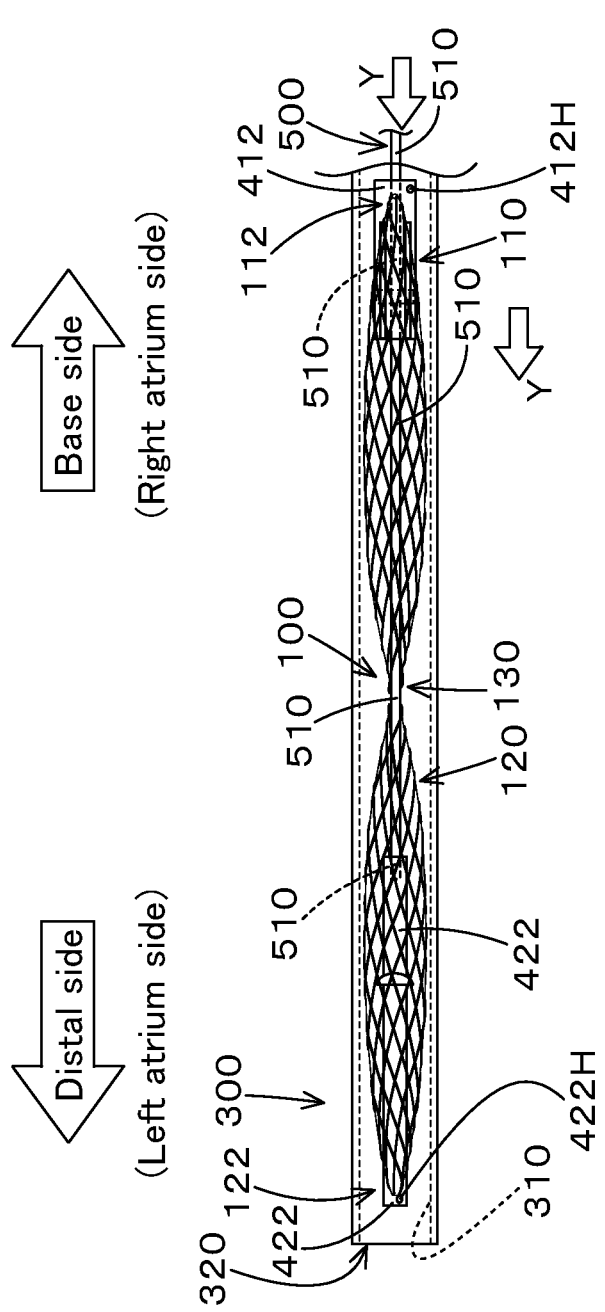
Figure 4:
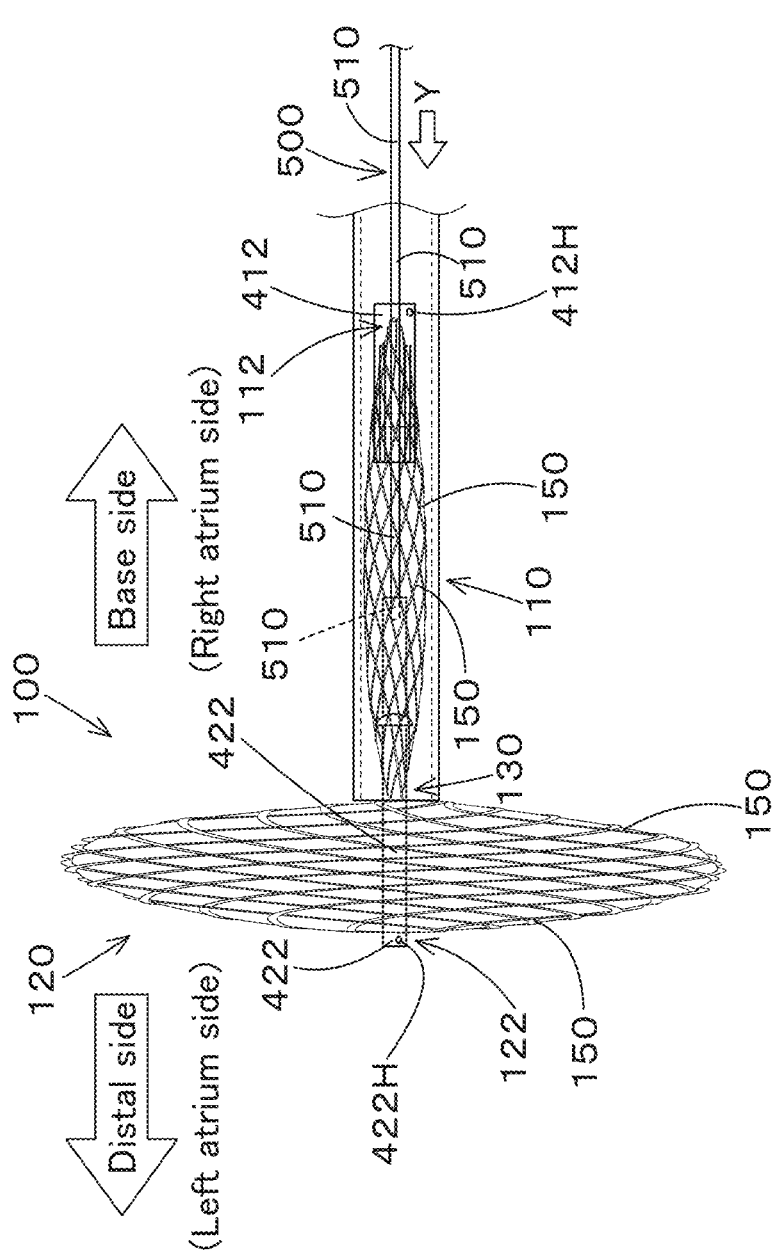
FIG. 4 is an overall view of a medical material 100 (in the state in which a second tubular portion has been moved out of the catheter 300 and a first tubular portion is contained in the catheter 300).

FIG. 1 shows an overall view of the medical material 100 according to the present embodiment (in the state in which a first end 112 and a second end 122 are close to each other), FIG. 2 shows another overall view of the medical material 100 (the distance between the first end 112 and the second end 122 is in an intermediate state), FIG. 3 shows a further overall view of the medical material 100 (the medical material 100 is entirely contained in a catheter 300, and the first end 112 and the second end 122 are away from each other), and FIG. 4 shows still a further overall view of the medical material 100 (in the state in which a second tubular portion 120 has been moved out of the catheter 300 and the first tubular portion 110 is contained in the catheter 300). Note that, with regard to the relationship between the medical material 100 and the catheter 300 in which the medical material 100 is contained, FIG. 3 illustrates the medical material 100 which is entirely contained in the catheter 300, and FIG. 4 illustrates the medical material 100 which is half (first tubular portion 110) contained in the catheter 300.

Figure 5A:
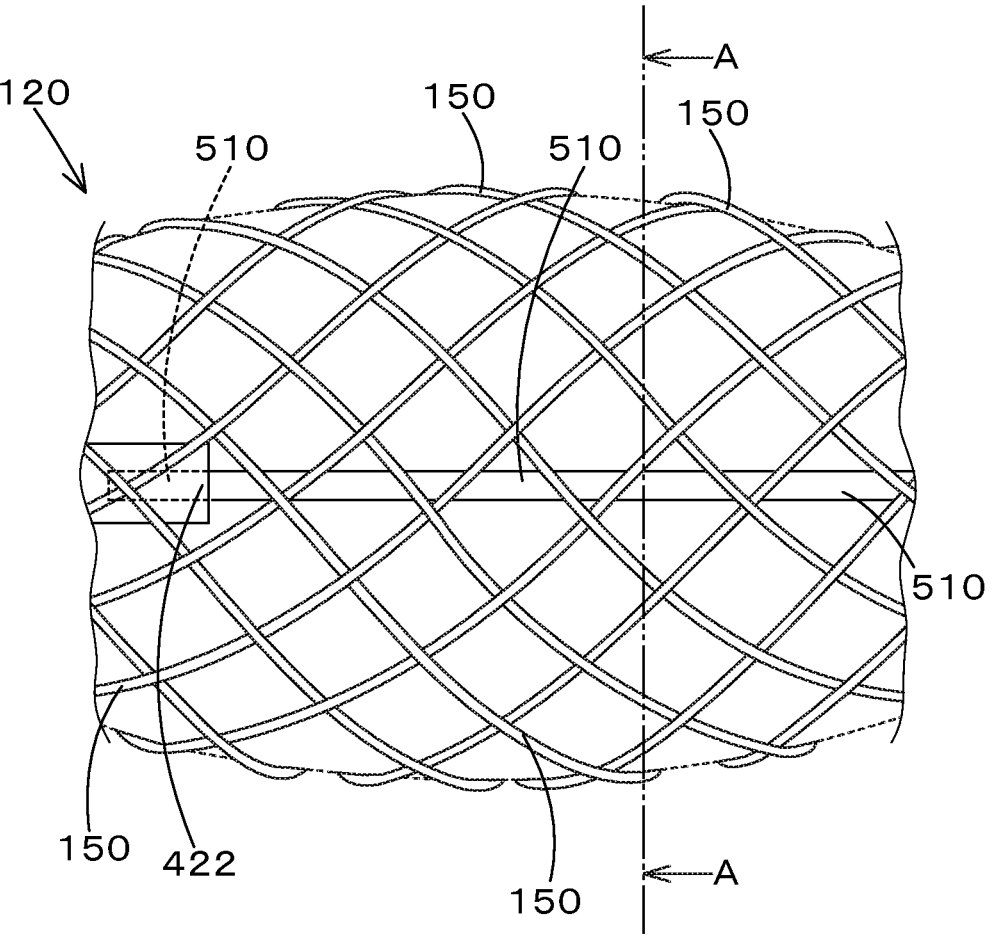
FIG. 5A is a partial side view of the medical material 100 in the state shown in FIG. 2.
Figure 5B:
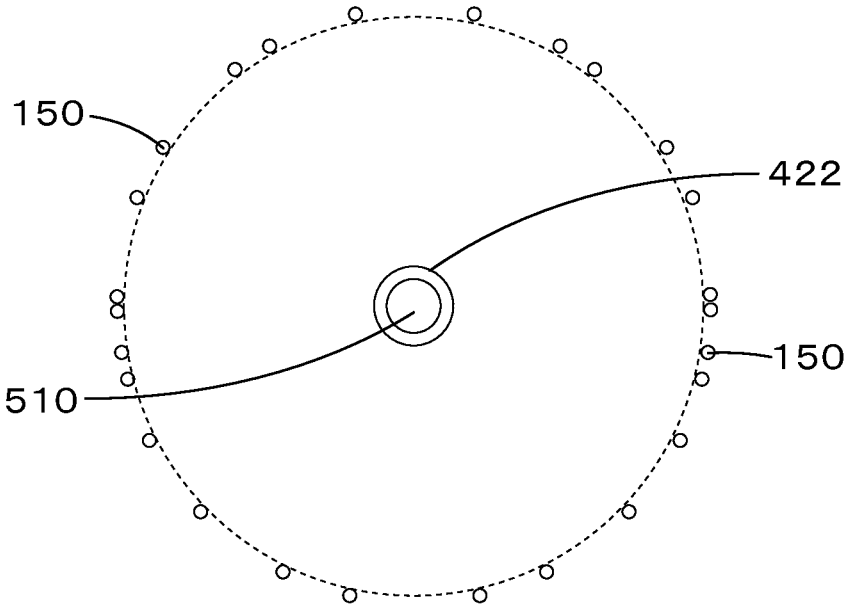
FIG. 5B is a cross-sectional view of the medical material 100 in the state shown in FIG. 2 taken along A-A.

In terms of temporal transition, when the second tubular portion 120 of the medical material 100 which is entirely contained in the catheter 300 (in the space defined by an inner wall 310) illustrated in FIG. 3 is allowed to move out through an opening 320 of the catheter 300 in the direction indicated by an arrow Y, the state of FIG. 4 results, and, when the first tubular portion 110 is also allowed to move out in the direction indicated by the arrow Y, the state of FIG. 1 results. It is noted here that the state of the medical material 100 illustrated in FIG. 2 is an imaginary state where the distance between the first end 112 and the second end 122 is in an intermediate state. FIG. 5A shows a partial side view of the medical material 100, and FIG. 5B shows a cross-sectional view taken along A-A in FIGS. 2 and 5A. Note that FIG. 5B is a cross-sectional view of the medical material 100 (more specifically, the second the tubular portion 120), but FIG. 5B illustrates a cross-section of a cable body 510 of a delivery cable 500 and does not illustrate the mesh of the bioabsorbable fiber 150 that is visually recognizable in the direction indicated by arrow A to show the direction of the cross-sectional view. FIGS. 10A to 11C each illustrate a distal connecting part 422 provided at the distal end (second end 122) of the medical material 100 and a proximal connecting part 412 provided at the proximal end (first end 112) of the medical material 100 and a delivery cable 500 which is screwed to the distal connecting part 422. Note that the terms "proximal" and "base" are synonymous.

It is noted there that the distal connecting part 422 can selectively achieve a connected state in which the distal connecting part 422 is connected to the distal end of the cable body 510 of the delivery cable 500 and a disconnected state in which the distal connecting part 422 is not connected to the distal end of the cable body 510. For example, the connected state is achieved in the following manner: the distal end of the cable body 510 of the delivery cable 500 is provided with an external thread, the distal connecting part 422 substantially in the shape of a cylinder is provided with an internal thread to be screwed onto the external thread (threads are not illustrated in FIG. 10A), and the internal thread and the external thread are screwed together. The disconnected state can be achieved by unscrewing the threads from each other.

As illustrated in FIGS. 1 to 5B and FIGS. 10A to 11C, an overview of the medical material 100 is as follows: the medical material 100 includes a tubular body having a mesh structure formed of a linear material and including a substantially middle portion and two tubular portions, the medical material 100 has a shape in which the substantially middle portion 130 of the tubular body is smaller in tube diameter than other portions of the tubular body, the medical material 100 includes the first tubular portion 110 with a first end 112 and the second tubular portion 120 with an opposite end (second end 122) which are arranged with the substantially middle portion 130 therebetween, the first end 112 and the second end 122 being opposite ends of the medical material 100 in a longitudinal direction of the tubular body.

The medical material 100 is characterized in that, when the medical material 100 is contained in the catheter 300 such that the first end 112 and the second end 122 are away from each other with the substantially middle portion 130 therebetween and the other portions have a reduced tube diameter (the state illustrated in FIG. 3), the second end 122 is located on the same side of the catheter 300 as the distal end of the catheter 300. In such a case, the medical material 100 includes: the proximal connecting part 412 connected to the mesh structure at the first end 112; and the distal connecting part 422 connected to the mesh structure at the second end 122. Note that, for non-limiting example, a part of the bioabsorbable fiber 150 that defines the first tubular portion 110 is passed through a hole 412H in the proximal connecting part 412 and the part of the bioabsorbable fiber 150 thus passed through the hole 412H is tied together with another part of the bioabsorbable fiber 150 that is not passed through the hole 412H, thus connecting the proximal connecting part 412 to the mesh structure at the first end 112, and, for non-limiting example, a part of the bioabsorbable fiber 150 that defines the second tubular portion 120 is passed through a hole 422H in the distal connecting part 422 and the part of the bioabsorbable fiber 150 thus passed through the hole 422H is tied together with another part of the bioabsorbable fiber 150 that is not passed through the hole 422H1, thus connecting the distal connecting part 422 to the mesh structure at the second end 122. Note that the number of holes 412H and 422H is not limited, but four holes 412H and hour hole 422H are provided.

It is noted here that the distal connecting part 422 is configured to selectively achieve a connected state in which the distal connecting part 422 is connected to the distal end of the delivery cable 500 and a disconnected state in which the distal connecting part 422 is not connected to the delivery cable 500. The medical material 100 is configured to allow the delivery cable 500, which has the distal end thereof connected to the distal connecting part 422, to extend through the substantially middle portion 130, be inserted into a hollow cylinder of the proximal connecting part 412, and extend out of the medical material 100 in a direction from the second end 122 to the first end 112 (for example, the first end 112 has a hole that allows passage of the cable body 510 of the delivery cable 500).

Characteristic features of the medical material 100 are detailed below mainly with reference to FIGS. 10A to 11C.

As shown in FIGS. 10A to 11C, the proximal connecting part 412 is substantially in the shape of a hollow cylinder, the distal connecting part 422 is substantially in the shape of a cylinder, and the proximal connecting part 412 and the distal connecting part 422 are configured such that the cylinder of the distal connecting part 422 is insertable into the hollow cylinder of the proximal connecting part 412. The medical material 100 is capable of reversibly or irreversibly achieving a locked in which in which such proximal connecting part 412 and distal connecting part 422 remain united and an unlocked state in which such proximal connecting part 412 and distal connecting part 422 do not remain united. To achieve such locked/unlocked states reversibly or irreversibly, such proximal connecting part 412 and distal connecting part 422 include the following configuration. The inner diameter of the proximal connecting part 412, which is substantially in the shape of a hollow cylinder, is larger than the outer diameter of the delivery cable 500 to be inserted into the catheter 300. The delivery cable is configured such that the delivery cable having connected thereto the distal connecting part is allowed to extend through the substantially middle portion, be inserted into the hollow cylinder of the proximal connecting part, and extend out of the medical material in the direction from the second end to the first end. The distal connecting part 422 substantially in the shape of a cylinder includes a radially outer portion 422A which is larger than the outer diameter of the delivery cable 500 but smaller than the inner diameter of the proximal connecting part 412 and an engaging portion 422C which is larger than the outer diameter of the radially outer portion 422A. The proximal connecting part 412 includes a radially inner portion 412A that fits the radially outer portion 422A and an engaged portion 412C which is larger than the inner diameter of the radially inner portion 412A and fits the engaging portion 422C. It is noted here that the phrase "the radially inner portion 412A of the proximal connecting part 412 fits the radially outer portion 422A" indicates that at least the inner diameter of the radially inner portion 412A is larger than the outer diameter of the radially outer portion 422A and that the radially outer portion 422A of the distal connecting part 422 can be inserted into the radially inner portion 412A of the proximal connecting part 412. The phrase "the engaged portion 412C of the proximal connecting part 412 fits the engaging portion 422C" indicates that the external shape (concave) of the engaged portion 412C is at least the same as or slightly larger than the external shape (convex) of the engaging portion 422C and that the engaging portion 422C of the distal connecting part 422 engages with the engaged portion 412C of the proximal connecting part 412 (the engaging portion 422C is blocked and stopped by the engaged portion 412C). When the distal connecting part 422 is inserted into the proximal connecting part 412, the engaging portion 422C of the distal connecting part 422 engages with the engaged portion 412C of the proximal connecting part 412, causing the medical material 100 to transition from the unlocked state to the locked state.

It is noted here that the proximal connecting part 412 is preferably expandable (has expandability) such that the inner diameter of a portion closer to the distal connecting part 422 than the other portion of the proximal connecting part 412 expands when the engaging portion 422C is inserted into the radially inner portion 412A and that the expanded inner diameter is de-expanded when the engaging portion 422C engages with the engaged portion 412C.

With regard to the expandability here, the following configuration may be used as the proximal connecting part 412 substantially in the shape of a hollow cylinder, for example. For example, the expandability can be achieved by providing the proximal connecting part 412 with one or more grooves 412B which connect the outer and inner surfaces of the hollow cylinder and which extend along the longitudinal direction of the delivery cable 500 from the end face facing the distal connecting part 422 to a predetermined location short of the end face at the first end 112 (proximal end). It is noted here that four grooves 412B are provided in a plane perpendicular to the longitudinal direction of the delivery cable 500 such that they are line-symmetric and point-symmetric with each other. It is preferable that the above-described predetermined location be closer to the proximal end (first end 112) than the engaged portion 412C is, in view of achieving good expandability.

The engaging portion 422C of the distal connecting part 422 and/or the engaged portion 412C of the proximal connecting part 412 (the engaging portion 422C of the distal connecting part 422 and the engaged portion 412C of the proximal connecting part 412 are discussed here, but only one of them may suffice) are preferably shaped to (have a shape to) provide a greater resistance to relative movement of the proximal connecting part 412 and the distal connecting part 422 during a transition from the locked state to the unlocked state in which the distal connecting part 422 is removed from the proximal connecting part 412 than during a transition from the unlocked state to the locked state in which the distal connecting part 422 is inserted into the proximal connecting part 412, in terms of easily maintaining the locked state. In order to cause the resistance to the relative movement to differ in such a manner, such a shape can include the following configuration. For example, the engaging portion 422C of the distal connecting part 422 and/or the engaged portion 412C of the proximal connecting part 412 may be shaped such that a proximal portion (a portion closer to the first end 112) thereof is smoother in shape than a distal portion (a portion closer to the second end 122) thereof. More specifically, as shown in FIGS. 10A to 11C, the proximal portion (portion closer to the first end 112 may include a curved shape 412C1 or a curved shape 422C1, and the distal portion (portion closer to the second end 122) may include a flat shape 412C2 or a flat shape 422C2.

These features are summarized and described below.

The medical material 100 according to the present embodiment includes the following configuration so that the proximal connecting part 412 and the distal connecting part 422 can reversibly or irreversibly achieve a locked state in which the proximal connecting part 412 and the distal connecting part 422 remain united and an unlocked state in which the proximal connecting part 412 and the distal connecting part 422 remain do not remain united.

The mechanism of the locking/unlocking structure of the medical material 100 is achieved in the following manner. The distal connecting part 422 provided at the left atrium side (distal side, the second end 122 side) of the tubular body of the mesh structure, and the proximal connecting part 412 provided at the right atrium side (proximal side, the first end 112 side) of the tubular body of the mesh structure, are configured such that, when the distal connecting part 422 is inserted into the proximal connecting part 412, the engaging portion 422C of the distal connecting part 422 engages with the engaged portion 412C of the proximal connecting part 412 to cause a transition of the medical material 100 from the unlocked state to the locked state.

Figure 10A:
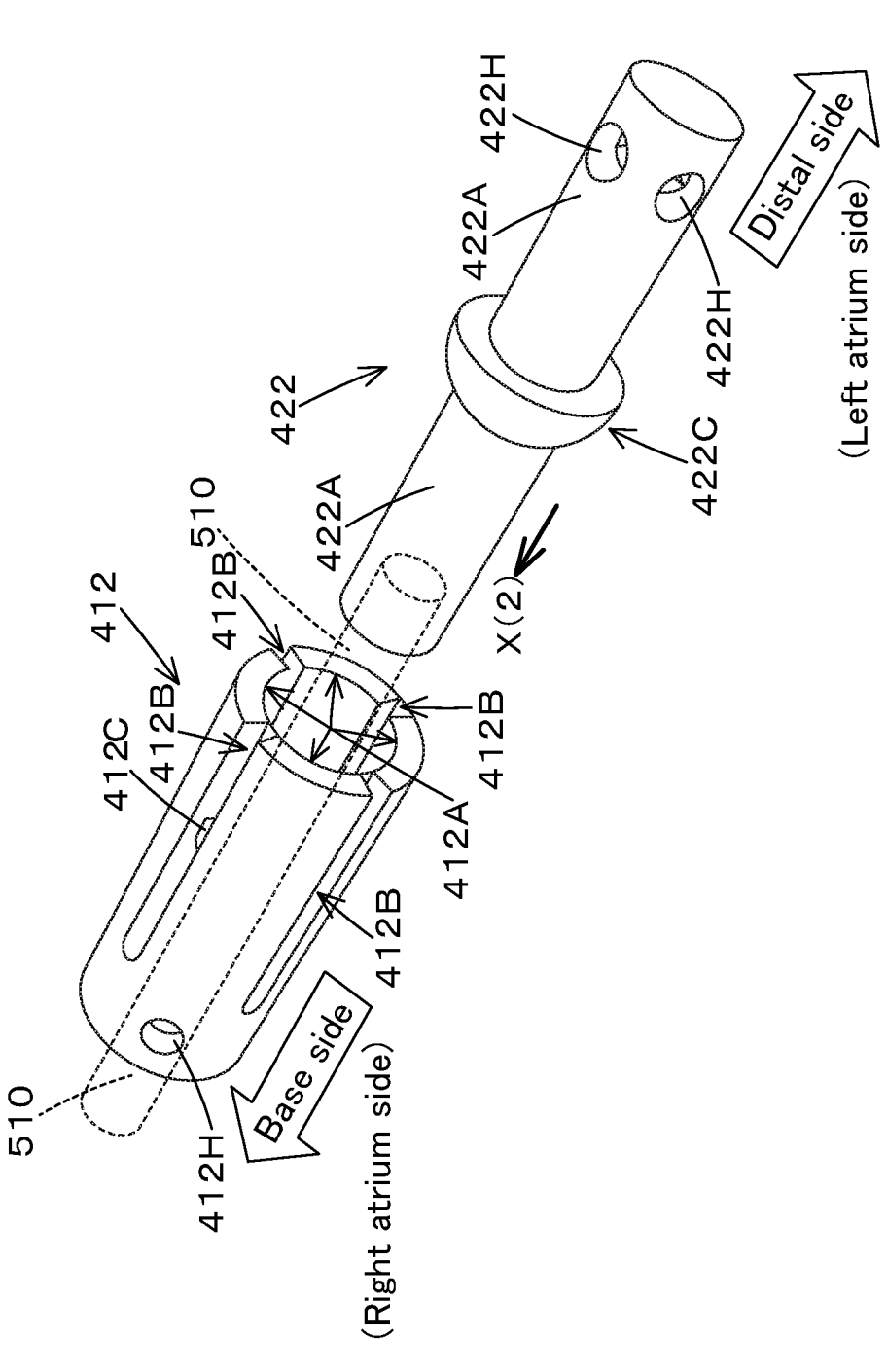
FIG. 10A is a perspective view (1) illustrating a distal connecting part 422 provided at the distal end (second end 122) of a medical material 100 and a proximal connecting part 412 provided at the proximal end (first end 112) of the medical material 100.
Figure 10B:
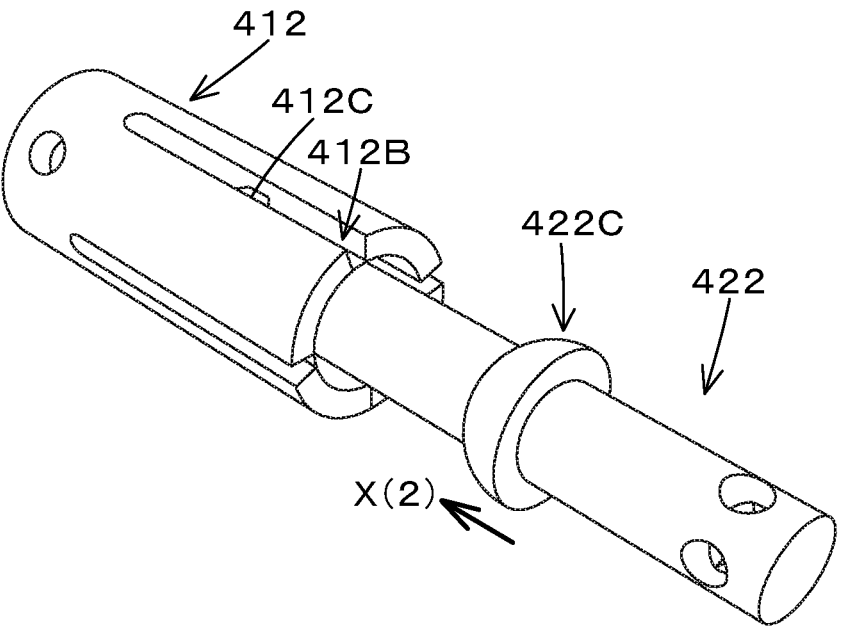
FIG. 10B is a perspective view (2) illustrating a distal connecting part 422 provided at the distal end (second end 122) of a medical material 100 and a proximal connecting part 412 provided at the proximal end (first end 112) of the medical material 100.
Figure 10C:
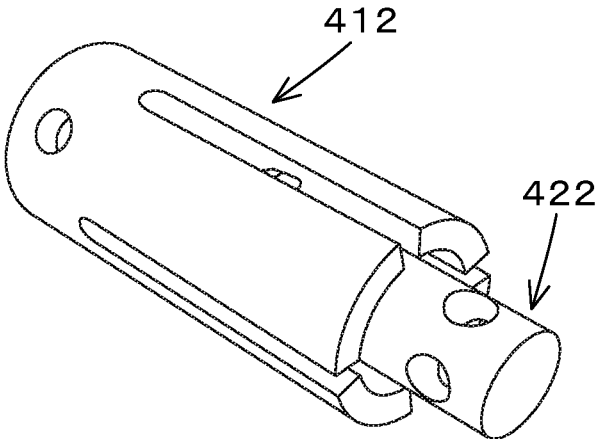
FIG. 10C is a perspective view (3) illustrating a distal connecting part 422 provided at the distal end (second end 122) of a medical material 100 and a proximal connecting part 412 provided at the proximal end (first end 112) of the medical material 100.
Figure 11A:
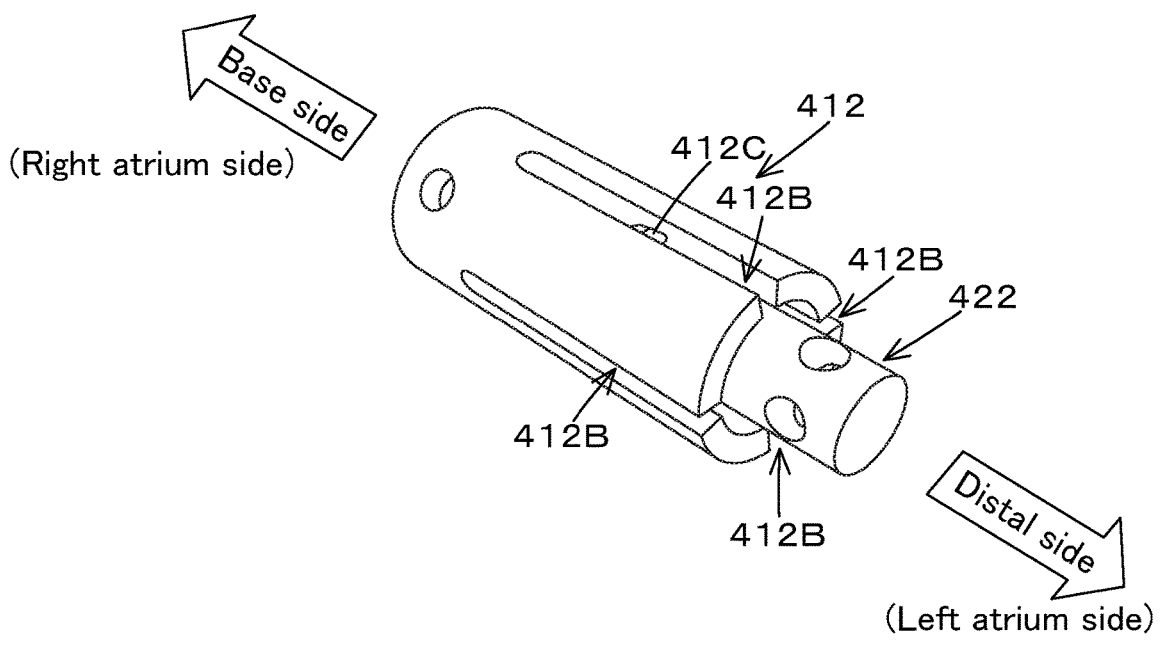
FIG. 11A is an illustration (1) including a cross-section of FIGS. 10A to 10C.
Figure 11B:
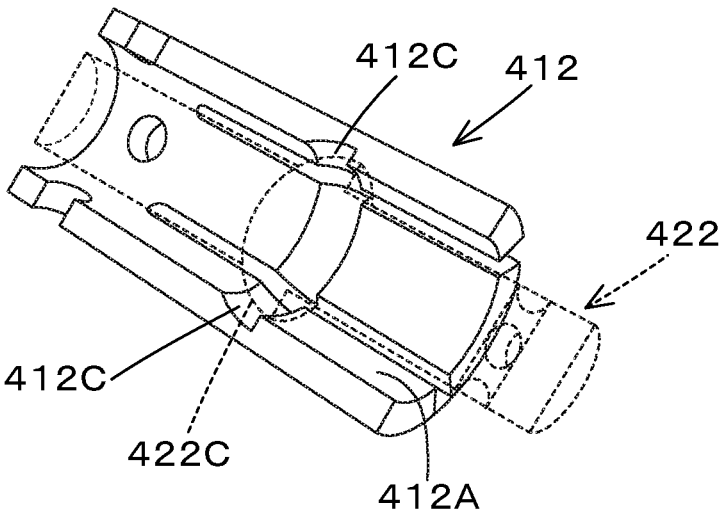
FIG. 11B is an illustration (2) including a cross-section of FIGS. 10A to 10C.
Figure 11C:
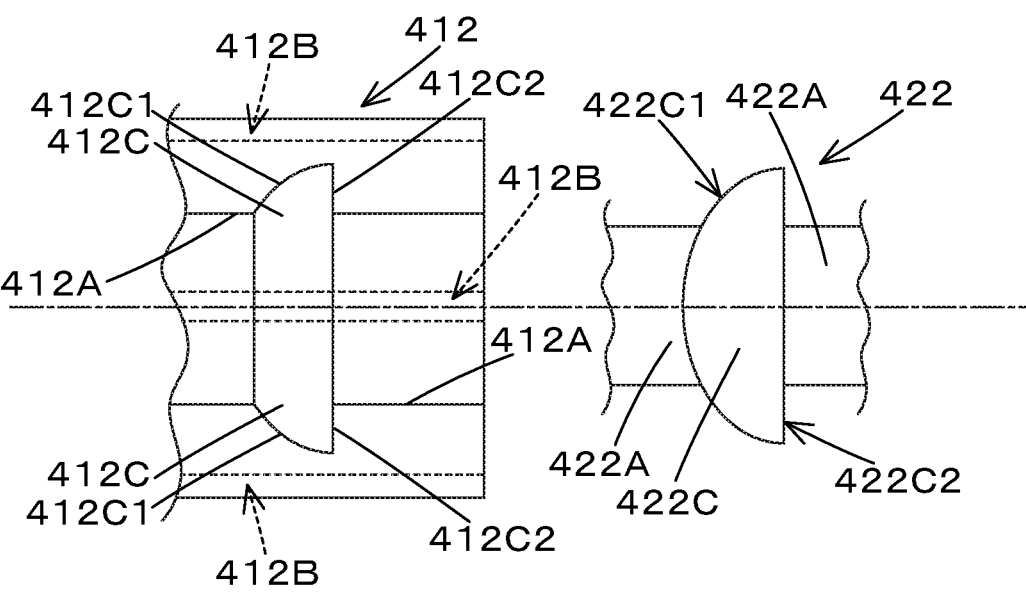
FIG. 11C is an illustration (3) including a cross-section of FIGS. 10A to 10C.

More specifically, the following is satisfied: (outer diameter of the delivery cable 500<) outer diameter of the radially outer portion 422A of the distal connecting part 422<the inner diameter of the radially inner portion 412A of the proximal connecting part 412<outer diameter of the engaging portion 422C of the distal connecting part 422<the inner diameter of the engaged portion 412C of the proximal connecting part 412 (<outer diameter of the proximal connecting part 412<inner diameter of the catheter 300). First, as shown in FIG. 10A, the radially outer portion 422A of the distal connecting part 422 starts to enter the radially inner portion 412A of the proximal connecting part 412 (the direction of entry is in the direction of arrow X (2)) to cause a transition to the state shown in FIG. 10B. From the state shown in FIG. 10B, when the radially outer portion 422A of the distal connecting part 422 further enters the radially inner portion 412A of the proximal connecting part 412, i.e., when the engaging portion 422C of the distal connecting part 422 starts to enter the radially inner portion 412A of the proximal connecting part 412, the expandability achieved by widening of the grooves 412B of the proximal connecting part 412 allows deformation such that the radially inner portion 412A of the proximal connecting part 412 becomes larger, and the inner diameter of the radially inner portion 412A expands (inner diameter of the radially inner portion 412A of the proximal connecting part 412~outer diameter of the engaging portion 422C of the distal connecting part 422). Note that, for example, a material with flexibility is suitably used so that the proximal connecting part 412 is not destroyed even when the inner diameter of the radially inner portion 412A expands in this manner.

When the radially outer portion 422A of the distal connecting part 422 further enters the radially inner portion 412A of the proximal connecting part 412, the engaging portion 422C of the distal connecting part 422 engages with the engaged portion 412C of the proximal connecting part 412, and the expanded inner diameter of the radially inner portion 412A is de-expanded, so that the medical material 100 transitions from the unlocked state to the locked state.

Furthermore, for non-limiting example, it is preferable that the proximal portions (portions each closer to the first end 112) include a curved surface 412C1 and a curved surface 422C1 (both of which are hemispherical (dome-shaped)) and that the distal portions (portions each closer to the second end 122) include a flat surface 412C2 and a flat surface 422C2, because, once a transition has occurred from the unlocked state to the locked state, the locked state is unlikely to transition to the unlocked state and therefore the medical material 100 set in the hole does not come off accidentally. It is not essential that such shapes of the engaging portion 422C and the engaged portion 412C be hemispherical. It is preferable that the engaging portion 422C and the engaged portion 412C be spherical or the like to achieve the locked and unlocked states reversibly.

Note that the raw material (material) for the proximal connecting part 412 and the distal connecting part 422 is not particularly limited, provided that the configuration or functions described above can be achieved. The material may be metal, resin, bioabsorbable material, and/or any other material.

It is noted here that the lengths in the longitudinal direction (the same as the longitudinal direction of the cable body 510 of the delivery cable 500) of the distal connecting part 422 and the proximal connecting part 412 as illustrated are merely examples and are not limited, provided that the unlocked and locked states can be achieved reversibly or irreversibly. The lengths are appropriately selected.

Another option would be to, in the situation shown in FIG. 1, change the length of the substantially middle portion 130 (which is also the distance between the first end 112 and the second end 122) depending on the thickness of the atrial septum that varies from individual to individual, and further set the lengths in the longitudinal direction of the distal connecting part 422 and the proximal connecting part 412 so that the distal connecting part 422 and the proximal connecting part 412 can be locked together at closer positions to each other when the atrial septum is thin than when it is thick and at positions farther away from each other when the atrial septum is thick than when it is thin.

The medical material 100 is configured to achieve the following. While the medical material 100 in which the distal end of the delivery cable 500 is connected to the second end 122 by the distal connecting part 422 is entirely contained in the catheter 300, the delivery cable 500 is manipulated, and the second tubular portion 120 is allowed to move out of the catheter 300 through the distal end of the catheter 300 and then the first tubular portion 110 is allowed to move out of the catheter 300 through the distal end of the catheter 300 such that the medical material 100 advances in the direction toward the opening of the catheter 300, so that the first end 112 and the second end 122 come close to each other with the substantially middle portion 130 therebetween. The delivery cable 500 is further manipulated and the proximal connecting part 412 and the distal connecting part 422 are united as described earlier and locked so that the proximal connecting part 412 and the distal connecting part 422 remain united, thereby maintaining a state in which the other portions have a tube diameter increased to a size corresponding to the hole to be closed with the medical material 100. The delivery cable 500 is further manipulated, the distal connecting part 422 and the distal end of the delivery cable 500 are brought from the connected state into the disconnected state, and the catheter 300, together with the delivery cable 500 inserted in the catheter 300, is separated from the site where there is the hole.

Such steps can be described with reference to FIGS. 6 to 9 when, for example, the medical material 100 is used in catheterization for atrial septal defect. Note, however, that such use embodiments of the medical material 100 described with reference to FIGS. 6 to 9 of the present application are the same as the descriptions for FIGS. 6 to 9 of Japanese Unexamined Patent Application Publication No. 2021-053267 (Patent Literature 1 in the present application), PCT International Application Publication No. 2016-174972 (and the specification of its corresponding U.S. Patent Application Publication No. 2018/0103956A1), and PCT International Application Publication No. 2020-012728 (and the specification of its corresponding U.S. Patent Application Publication No. 2021/0169497A1) which are filed by the applicant of the present application, except for the structures of the distal connecting part 422 and the proximal connecting part 412 that can achieve the locked and unlocked states reversibly or irreversibly. Therefore, the embodiments are not detailed here.

Figure 6:
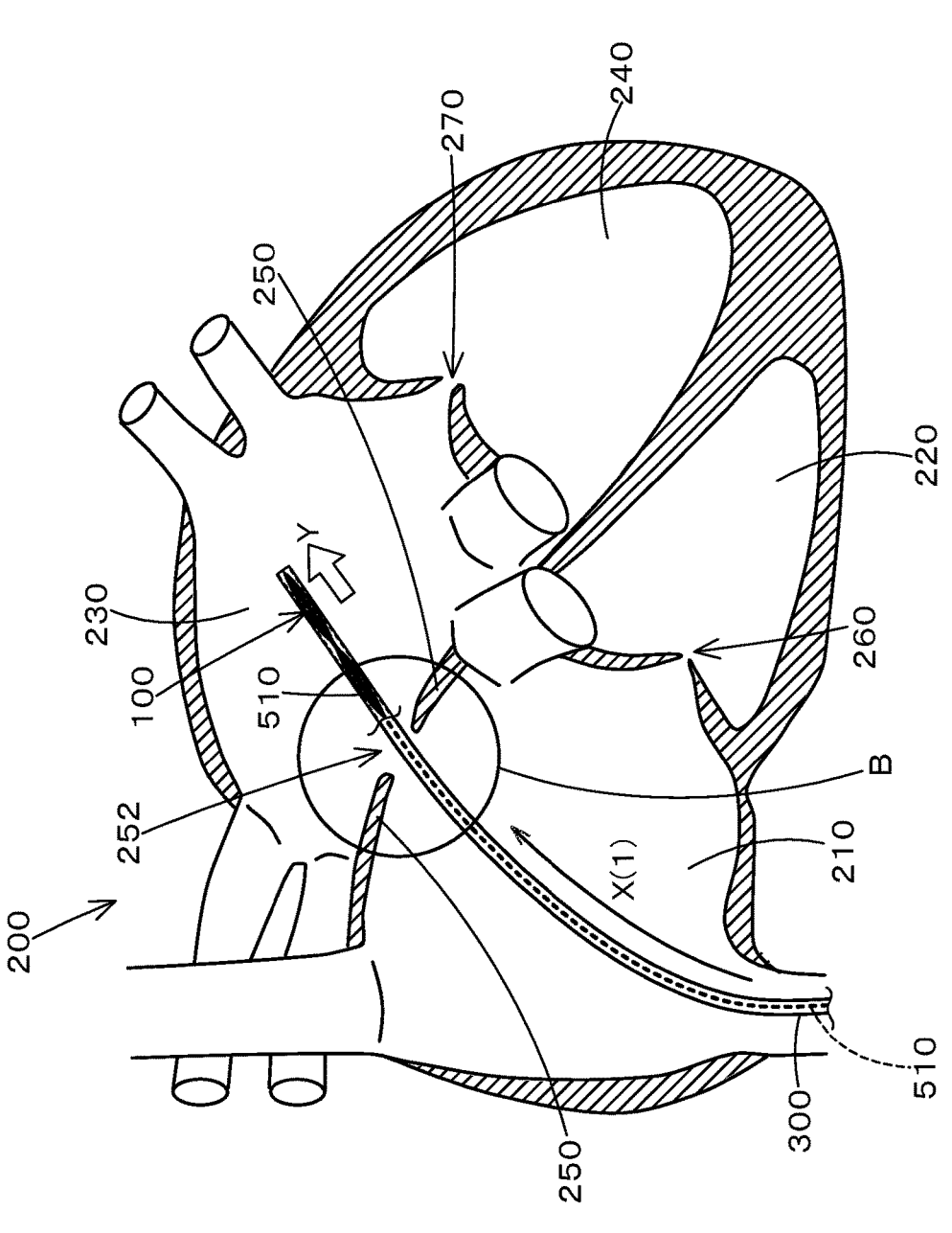
FIG. 6 is a conceptual view in which a medical material 100 is used in catheterization for atrial septal defect.
Figure 7:
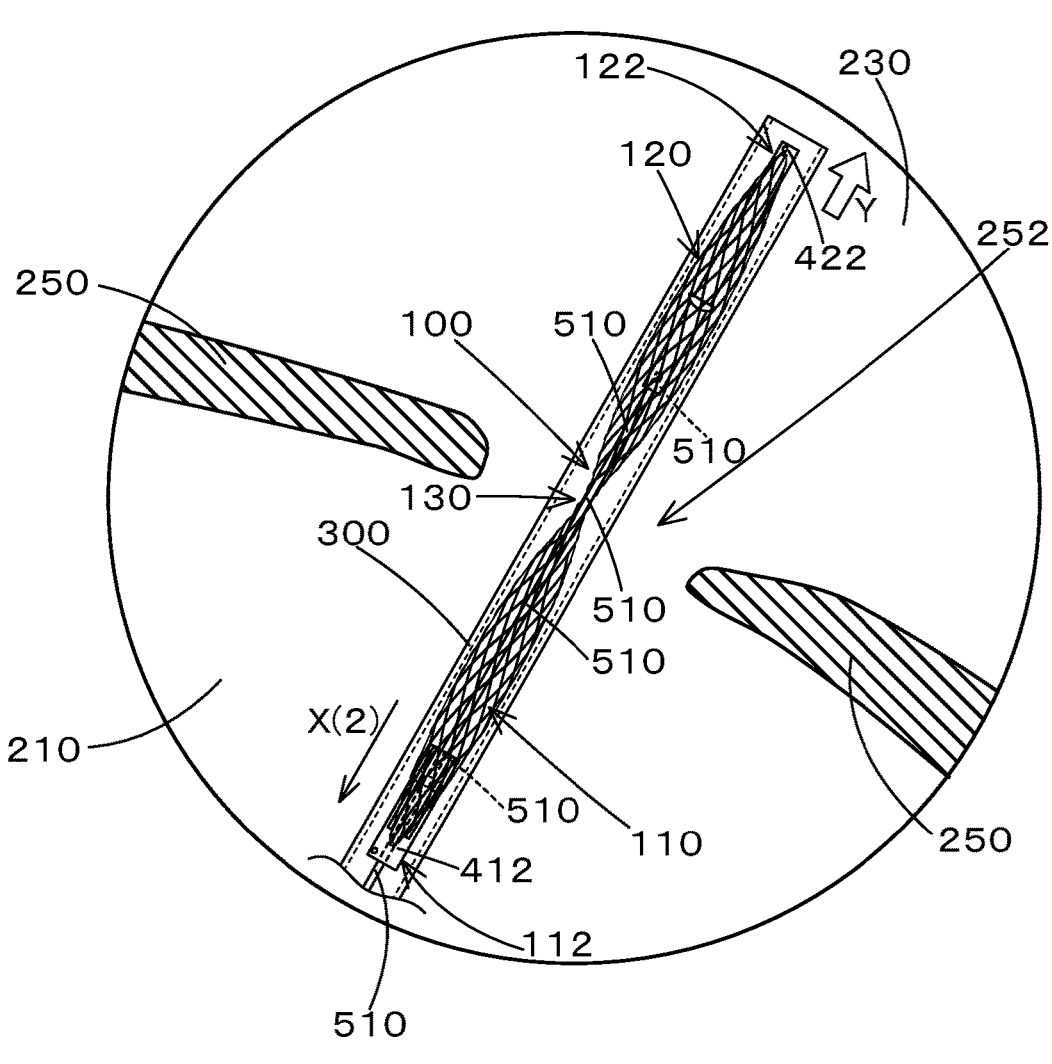
FIG. 7 is an enlarged view (1) of part B in FIG. 6 illustrating a procedure of catheterization.
Figure 8:
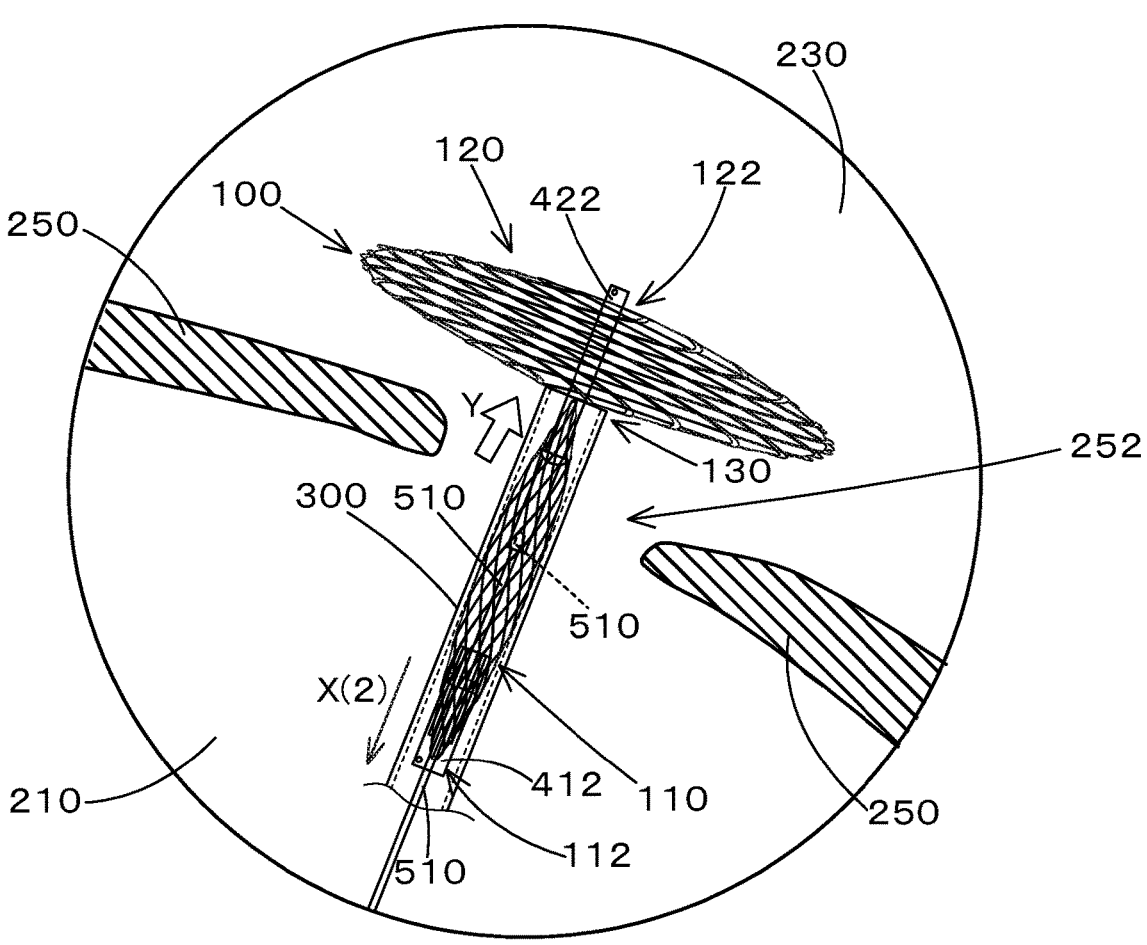
FIG. 8 is an enlarged view (2) of part B in FIG. 6 illustrating the procedure of catheterization.

It is noted here that the state of the medical material 100 in FIGS. 6 and 7 is the state in FIG. 3 (unlocked state), the state of the medical material 100 in FIG. 8 is the state in FIG.

Figure 9:
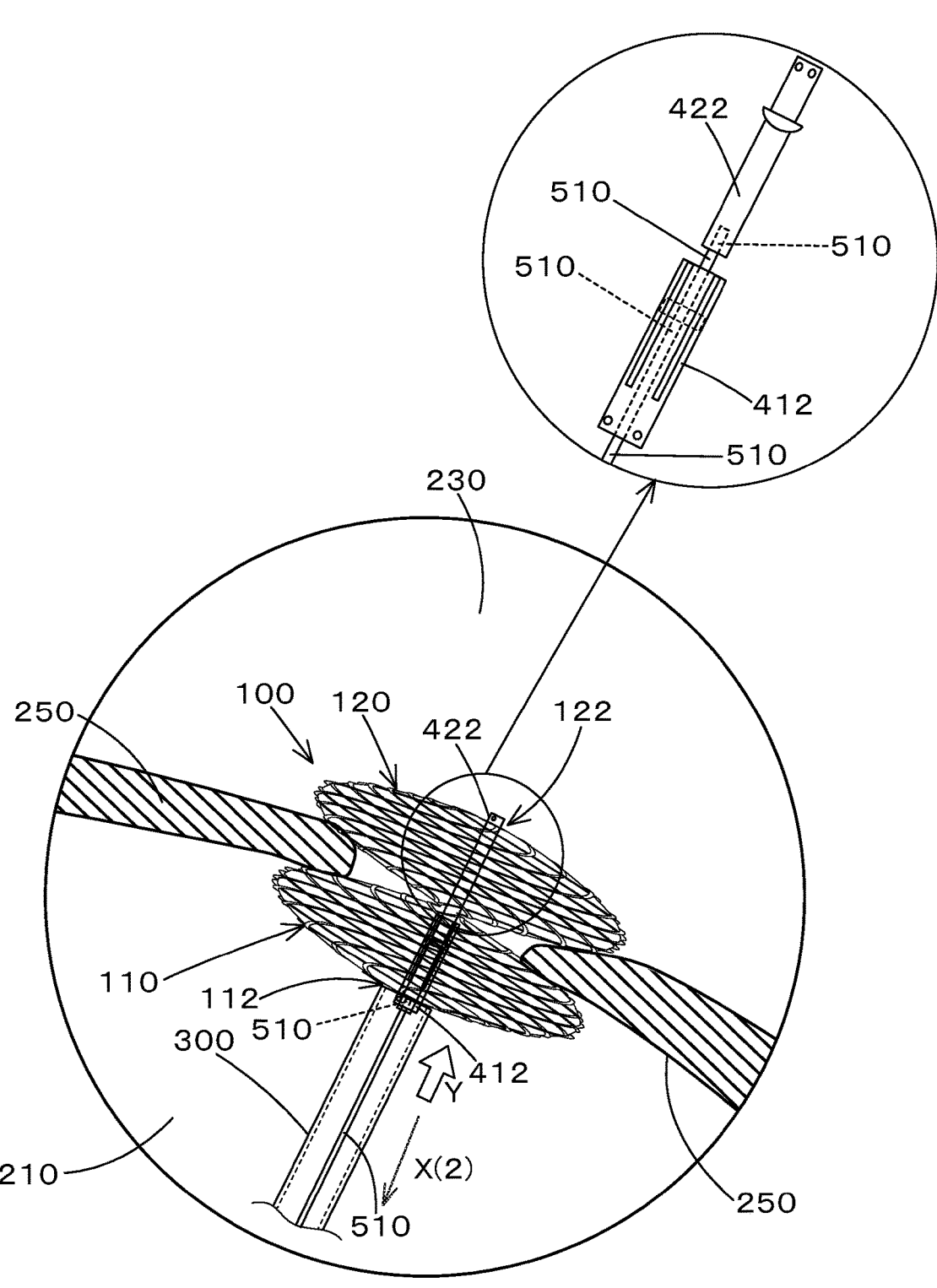
FIG. 9 is an enlarged view (3) of part B in FIG. 6 illustrating the procedure of catheterization.

4 (unlocked state), and the state of the medical material 100 in FIG. 9 is the state in FIG. 1 (locked state).

As has been described, with the medical material 100 according to the present embodiment, it is possible to provide a medical material which makes it possible to perform less invasive catheterization capable of releasing and placing the medical material at a treatment site inside a living body with easy and reliable operation without a complicated structure (which makes it possible to achieve locked/unlocked states reversibly or irreversibly).

Note that it is to be understood that embodiments disclosed herein are considered as examples in all aspects and are not considered as limitations. The scope of the present invention is to be determined not by the foregoing description but by the claims, and is intended to include all variations and modifications within the scope of the claims and their equivalents.

Industrial Applicability

The present invention is suitable for use as a medical material which is set in a catheter to treat a hole in a biological tissue, and is particularly preferable in that the medical material is capable of being released and placed at a treatment site, enables less invasive treatment, is unlikely to cause a problem in the late post-treatment period even when the medical material remains in the body, and is favorably operable.

REFERENCE SIGNS LIST

100 Medical material (occluder)
110 First tubular portion
112 First end
120 Second tubular portion
122 Second end
130 Substantially middle portion
150 Bioabsorbable fiber
200 Heart
250 Atrial septum
252 Hole
300 Catheter
412 Proximal connecting part
422 Distal connecting part
500 Delivery cable (manipulation wire)

The invention claimed is:

1. A medical material comprising a tubular body having a mesh structure formed of a bioabsorbable linear material and including a substantially middle portion and two tubular portions, the two tubular portions including a first tubular portion and a second tubular portion between which the substantially middle portion is provided; wherein the substantially middle portion is smaller in tube diameter than other portions;

the first tubular portion with a first end and the second tubular portion with a second end are arranged with the substantially middle portion therebetween, the first end and the second end being opposite ends in a longitudinal direction of the tubular body;

when the medical material is contained in a catheter such that the first end and the second end are away from each other with the substantially middle portion therebetween and that the other portions have a reduced tube diameter, the second end is located on the same side of the catheter as a distal end of the catheter;

the medical material includes:

a proximal connecting part connected to the mesh structure at the first end; and a distal connecting part connected to the mesh structure at the second end;

the proximal connecting part is substantially in a shape of a hollow cylinder, the distal connecting part is substantially in a shape of a cylinder, the proximal connecting part and the distal connecting part are configured such that the cylinder of the distal connecting part is insertable into the hollow cylinder of the proximal connecting part, and are configured to reversibly or irreversibly achieve a locked state and an unlocked state, the locked state being a state in which the proximal connecting part and the distal connecting part remain united, the unlocked state being a state in which the proximal connecting part and the distal connecting part do not remain united;

an inner diameter of the proximal connecting part is larger than an outer diameter of a delivery cable to be inserted into the catheter;

the distal connecting part is configured to selectively achieve a connected state in which the distal connecting part is connected to a distal end of the delivery cable and a disconnected state in which the distal connecting part is not connected to the distal end of the delivery cable;

the medical material is configured to allow the delivery cable, which has the distal end thereof connected to the distal connecting part, to extend through the substantially middle portion, be inserted into the hollow cylinder of the proximal connecting part, and extend out of the medical material in a direction from the second end to the first end;

the distal connecting part includes:

a radially outer portion larger than an outer diameter of the delivery cable and smaller than the inner diameter of the proximal connecting part; and an engaging portion larger than an outer diameter of the radially outer portion;

the proximal connecting part includes:

a radially inner portion which fits the radially outer portion; and an engaged portion which is larger than an inner diameter of the radially inner portion and which fits the engaging portion;

when the distal connecting part is inserted into the proximal connecting part, the engaging portion of the distal connecting part engages with the engaged portion of the proximal connecting part to cause a transition from the unlocked state to the locked state;

the medical material includes the delivery cable;

the proximal connecting part has expandability such that the inner diameter of a portion closer to the distal connecting part than the other portion of the proximal connecting part expands when the engaging portion is inserted into the radially inner portion and that the expanded inner diameter is de-expanded when the engaging portion engages with the engaged portion; and the proximal connecting part, which is substantially in the shape of the hollow cylinder, achieves the expandability thereof by having four grooves which are spaced substantially 90 degrees apart from each other, which connect outer and inner surfaces of the hollow cylinder, and each of which extends along a longitudinal direction of the delivery cable from an end face facing the distal connecting part to a predetermined location short of an end face at the first end.

* * * * *